(12) United States Patent
Birkel et al.

(10) Patent No.: US 6,475,475 B2
(45) Date of Patent: Nov. 5, 2002

(54) POLYMER INGREDIENT COMBINATIONS FOR HAIR TREATMENT COMPOSITIONS

(75) Inventors: Susanne Birkel, Glashuetten (DE); Michael Lede, Langen (DE)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 09/729,014

(22) Filed: Dec. 4, 2000

(65) Prior Publication Data

US 2001/0003584 A1 Jun. 14, 2001

(30) Foreign Application Priority Data

Dec. 2, 1999 (DE) .......................... 199 57 947

(51) Int. Cl.[7] .............................. A61K 7/06; A61K 7/11; A61K 9/12; C08F 120/10; C08F 210/16
(52) U.S. Cl. ..................... 424/70.15; 424/47; 424/70.1; 424/70.11; 424/401; 424/DIG. 1; 424/DIG. 2; 514/772.1; 514/784; 514/880; 525/330.3; 525/7.1; 525/331.7; 525/73; 525/326.9
(58) Field of Search ................. 424/70.15, 47, 424/70.1, 70.11, 401, DIG. 1, DIG. 2; 514/772.1, 784, 880; 525/330.3, 7.1, 331.7, 73, 326.9

(56) References Cited

U.S. PATENT DOCUMENTS

| 5,053,218 A | | 10/1991 | Shernoy | |
|---|---|---|---|---|
| 5,266,308 A | | 11/1993 | Lee et al. | |
| 5,304,368 A | | 4/1994 | Shernov | |
| 5,626,836 A | * | 5/1997 | Liu et al. | ........................ 424/47 |
| 5,690,921 A | | 11/1997 | Lang et al. | |
| 6,156,298 A | * | 12/2000 | Karlen et al. | ............. 424/70.31 |
| 6,294,158 B1 | * | 9/2001 | Dupuis | ........................ 424/70.1 |
| 2001/0026791 A1 | * | 10/2001 | Lede et al. | ............... 424/70.15 |

FOREIGN PATENT DOCUMENTS

| WO | 96/00565 | 1/1996 |
|---|---|---|
| WO | 96/19971 | 7/1996 |
| WO | 96/20694 | 7/1996 |

OTHER PUBLICATIONS

F Frosch et al: "Assessment of Polymers for Hair Setting", Spray Technology & Marketing, May 1994, pp. 25–29.
F Frosch et al: "Une Methode Simple Pour Mesurer La Fixation Des Cheveux", Parfum, Cosmetiques, Aromes n. 89, Oct.–Nov. 1989, pp. 71–73.

* cited by examiner

*Primary Examiner*—Frederick Krass
*Assistant Examiner*—Clinton Ostrop
(74) *Attorney, Agent, or Firm*—Michael J. Striker

(57) ABSTRACT

Combinations of polymer compounds and hair treatment compositions containing them are described, which have improved film-forming properties and improved hair-fixing properties, particularly increased elasticity of the polymer film or the treated hair. The polymer compound combinations include at least one terpolymer of vinyl pyrrolidone, vinyl caprolactam and basic acryl amide monomer and at least one anionic or anionizable polymer with anionic or anionizable groups.

13 Claims, No Drawings ns with alkyl groups having from one to four carbon atoms and dialkylaminoalkylacrylamides with alkyl groups having from 1 to 4 carbon atoms. Dimethylaminopropyl-methacrylamides are especially preferred. The production of this sort of polymer is described in WO 96/19971 and it is commercially obtainable under the trademark AQUAFLEX® SF 40 (ISP) (INCI-name: PVP/vinyl caprolactam/DMAPA acrylates copolymer).

POLYMER INGREDIENT COMBINATIONS FOR HAIR TREATMENT COMPOSITIONS

BACKGROUND OF THE INVENTION

1. Field of the Invention

The subject matter of the present invention is a polymer combination, i.e. a combination of polymeric ingredients, and a hair treatment composition with a content of this polymeric combination. More particularly, the subject matter of the present invention is a hair treatment composition with a combination of at least one terpolymer selected from the group consisting of vinyl pyrrolidone, vinyl caprolactam and a basic acrylamide monomer as well as at least one polymer compound having an anionic or anionizable group.

2. Prior Art

In order to fix and hold human hair or to stabilize a hairstyle or hair-do hair treatment compositions in the form of fixing lotions, aerosol and non-aerosol sprays, fixing-foams, gels, etc, are used. The cosmetic hair-fixing polymers used for these purposes have good fixing properties in aqueous, alcoholic or aqueous-alcoholic media, which hold and fix the hair in its form more or less well and stabilize an established hairstyle. Frequency however the hair-do has a stiff and unnatural feel and the elasticity of the polymer film and the polymer-cross-linked hairstyle is insufficient.

Terpolymers of vinyl pyrrolidone, vinyl caprolactam and 3-(N-dimethyl-aminopropyl)methacrylamide are known from WO 96/19971. Their use in hair-fixing compositions, especially in aerosol and pump sprays, is also disclosed in WO 96/19971. These polymer compounds are especially suitable for use in an aqueous spray formulation with a reduced content of highly volatile organic ingredients (low VOC sprays). These polymer compounds have good fixing properties, but impart a comparatively rough and inelastic feel, as well as a comparatively high load, to the hair.

SUMMARY OF THE INVENTION

It is thus an object of the present invention to further improve the film-forming and hair-fixing properties of polymer-containing preparations and especially to increase the elasticity of polymer films and/or polymer-treated hair.

It has been found that this object is attained by a combination of two select polymer compounds or by a hair treatment composition containing this polymer combination.

The polymer combination according to the invention comprises
(A) at least one terpolymer of vinyl pyrrolidone, vinyl caprolactam and a basic acrylamide monomer, and
(B) at least one polymer with anionic or anionizable groups.

The subject matter of the invention also includes a hair treatment composition with a content of the above-named polymer combination in a suitable cosmetic base. The polymer combination according to the invention causes an increase, especially a synergistic increase, of the elasticity of the polymer film and/or the polymer treated hair.

The terpolymer (A) is present in the composition according to the invention, preferably, in an amount of 0.01 to 20, especially preferably of 0.05 to 10, and most preferably of 0.1 to 5, percent by weight and the anionic polymer (B) is present in an amount of from 0.01 to 20, especially preferably of 0.05 to 10, and most preferably from 0.1 to 5, percent by weight.

Suitable terpolymers (A) are those, in which the acrylamide monomer is selected from dialkylaminoalkylmethacrylamides with alkyl groups having from one to four carbon atoms and dialkylaminoalkylacrylamides with alkyl groups having from 1 to 4 carbon atoms. Dimethylaminopropyl-methacrylamides are especially preferred. The production of this sort of polymer is described in WO 96/19971 and it is commercially obtainable under the trademark AQUAFLEX® SF 40 (ISP) (INCI-name: PVP/vinyl caprolactam/DMAPA acrylates copolymer).

Polymer compound (B) can be an anionic polymer compound but also an amphoteric polymer compound, which has basic groups in the polymer molecule as well as anionic or anionizable groups.

For example, the anionizable groups can include acid groups, such as carboxylic acid, sulfonic or phosphoric acid groups, which can be deprotonated by common bases, such as organic amines or alkali or alkaline earth hydroxides.

The polymer compounds for ingredient (B) can be partially or completely neutralized with a basic neutralization agent. Those compounds, in which the acid groups are neutralized from 50 to 100%, especially from 70 to 100%, are particularly preferred. Organic or inorganic bases are used as neutralizing agents. For example, aminoalkanols, such as aminomethylpropanol (AMP), triethanolamine or monoethanolamines, also ammonia, NaOH and KOH, can be used as the base.

The polymer (B) can be a homopolymer or copolymer with monomer units containing acid groups on a natural or synthetic basis, which, if necessary, is polymerized with a comonomer, which does not contain acid groups. The acid groups can include sulfonic acid groups, phosphoric acid groups and carboxylic acid groups, of which the carboxylic acid groups are especially preferred. Suitable monomers containing acid groups include, for example, acrylic acid, methacrylic acid, crotonic acid, maleic acid and/or maleic acid anhydride, maleic acid monoester, especially the mono-C1- to C7-alkyl ester of the maleic acid and alkdehydocarboxylic acids or ketocarboxylic acids.

Comonomers not substituted with acid groups are, for example, acrylamides, methacrylamides, alkyl- an dialkylacrylamides, alkyl- and dialkylmethacrylamides, alkylacrylates, alkylmethacrylates, vinylcaprolactones, vinyl pyrrolidones, vinyl esters, vinyl alcohols, propylene glycols or ethylene glycols, amine-substituted vinyl monomers, such as dialkylaminoalkylacrylates, dialkylaminoalkylmethacrylates, monoalkylaminoalkylacrylates and monoalkylaminoalkylmethacrylates, in which the alkyl groups of these monomers, preferably C1- to C7-alkyl groups, especially preferably C1- to C3-alkyl groups.

Suitable polymer compounds with acid groups include especially uncross-linked homopolymers of acrylic acid or methacrylic acid or homopolymers of acrylic or methacrylic acid that are cross-linked with polyfunctional agents; copolymers of acrylic acid or methacrylic acid with monomers selected from the group consisting of acrylic acid esters, methacrylic acid esters, acrylamides, methacrylamides and vinylpyrrolidones; homopolymers of crotonic acid as well as copolymers of crotonic acid with monomers selected from the group consisting of vinyl esters, acrylic acid or methacrylic acid esters, acryl amides and methacrylamides. Shellac is, for example, a suitable natural polymer.

Suitable polymer compounds with acid groups include cross-linked or uncross-linked vinyl acetate/crotonic acid copolymers (INCI-name: VA/crotonate copolymers), vinyl acetate/crotonic acid/vinyl alkanoate copolymers (INCI-name: VA/crotonates/vinyl porpionate copolymer, VA/crotonates/vinyl neodecanoate copolymer), copolymers of one or more C1- to C5-alkylacrylates, especially C2-C4-alkylacrylates and acrylic acid or methacrylic acid (INCI-name: acrylate copolymers). Terpolymers of acrylic acid, alkylacrylates and N-alkylacrylamides, especially acrylic acid/ethylacrylates/N-t-butylacrylamides terpolymers (INCI-name: acrylates/acrylamide copolymers), copolymers of methyl vinyl ether and maleic acid monoalkyl esters (INCI-name: ethyl ester of PVM/MA copolymers, butyl esters of PVM/MA copolymer).

Additional preferred polymers with acid groups include amphoteric polymers, for example copolymer of alkylacrylamides, especially octylacrylamides, alkylaminoalkylmethacrylates, especially t-butylaminoethylmethacrylates and two or more monomers selected from the group consisting of acrylic acid, methacrylic acid or their esters (INCI-name: octylacrylamide/acrylates/butylaminoethyl methacrylate copolymers). Additional suitable amphoteric polymers include copolymers, which are formed from at least one first type of monomer, which has a quaternary amine group, and at least one second type of monomer, which has an acid group. For example, this sort of copolymer includes copolymers of acrylic acid, methylacrylate and methacrylamidopropyltrimethylammonium chloride (INCI-name: polyquaternium-47), copolymers of acrylamidopropyltrimethyl ammonium chloride and acrylates or copolymers of acrylamide, acrylamido propyltrimethyl ammonbium chloride , 2-amidopropylacrylamide sulfonate and dimethylaminopropylamies (INCI-name: poly-quaternium-43).

In a preferred embodiment the composition according to the invention also contains from 0.01 to 15 percent by weight, preferably from 0.5 to 10 percent by weight, of at least one synthetic or natural nonionic film-forming polymer. The term "natural polymers" is understood to mean chemically modified polymer compounds of natural origin. Those polymers are especially preferred, which have sufficient solubility in alcohol or water/alcohol mixture, in order to be present in completely dissolved form in the composition according to the invention. The term "film-forming polymers" means those polymers, which deposit a polymer film on the hair when used in a 0.01 to 5% aqueous, alcoholic or aqueous-alcoholic solution.

Suitable synthetic, nonionic, film-forming hair-fixing polymers include homo- or copolymers, which are built up from at least one of the following nonionic monomers: vinyl pyrrolidone, vinyl caprolactam, vinyl esters, such as vinyl acetate, vinyl alcohols, acryl amides, methacryl amides, alkyl- and dialkylacrylamides, alkyl- and dialkylmethacrylamides, alkylacrylates, alkylmethacrylates, propylene glycol or ethylene glycol, wherein the alkyl groups of these monomers preferably have from one to seven carbon atoms, especially preferably from one to three carbon atoms.

The homopolymers of vinyl caprolactames, vinyl pyrrolidones or N-vinyl formamides are e.g. suitable. Additional suitable synthetic film-forming non-ionic hair-fixing polymers include, e.g., copolymerizates of vinyl pyrrolidone and vinyl acetate, terpolymers of vinyl pyrrolidone, vinyl acetate and vinyl propionate. Polyacrylamides, which for example are marketed under the trademarks Akypomine® P191 of CHEM-Y, Emmerich, or Sepigel® 305 of Seppic; polyvinyl alcohols, which are sold under the trademark Elvanol® of DuPont or Vinol® 523/540 of Air Products; and Polyethylene glycol/polypropylene glycol copolymers, which for example are sold under the trademark Ucon® of Union Carbide. Polyvinyl pyrrolidone and polyvinyl pyrrolidone/vinyl acetate copolymers.

Suitable natural film-forming polymers are, e.g., cellulose derivatives, e.g. hydroxypropyl cellulose with a molecular weight of 30,000 to 50,000 g/mol, which, for example, is marketed under the tradmark NISSO SI® of Lehmann & Voss, Hamburg.

The composition according to the invention is preferably packaged in an aqueous, alcoholic or an aqueous-alcoholic medium preferably with at least 10 percent by weight water. Lower alcohols with 1 to 4 carbon atoms, such as ethanol and isopropanol, can be contained. The composition according to the invention can be present in a pH range of from 2.0 to 9.5. A pH range of from 2.5 to 8 is particularly preferred.

Organic solvents or a mixture of such solvent with a boiling point under 400° C. can be contained in the composition according to the invention in an amount of from 0.1 to 15 percent by weight, especially preferably of from 1 to 10 percent by weight, as additional co-solvents. Branched or unbranched hydrocarbons, such as pentane, hexane, isopentane and cyclic hydrocarbons, such as cyclopentane and cyclohexane, are especially suitable as co-solvents. Ethylene glycol, glycerol, and propylene glycol in amount of up to 30 percent by weight are especially preferred water-soluble solvents.

The composition according to the invention can also contain cosmetic additive ingredients commonly used in hair treatment compositions, for example wetting agents or emulsifiers from the classes of nonionic, anionic, cationic or amphoteric surface-active substances, such as fatty alcohol sulfates, alkylbenzene sulfonates, alkyltrimethyl ammonium salts, alkyl betaines, in an amount of from 0.1 to 15 percent by weight; moisturizing agents; perfumes, in an amount of from 0.1 to 0.5 percent by weight; turbidity-inducing agents, such as ethylene glycol distearates, in an amount of about 0.2 to 5.0 percent by weight; pearlescence-inducing agents, for example a mixture of fatty acid monoalkylol amides and ethylene glycol distearates, in an amount of from about 1.0 to 10 percent by weight; bactericide and fungicidal substances, for example, 2,4,4-trichloro-2-hydroxydiphenyl ether or methyl chloroisothiazolione, in an amount of from 0.01 to 1.0 percent by weight; thickeners, for example coconut oil fatty acid diethanolamide, in an amount of about 0.2 to 3.0 percent by weight; buffer substances, such as sodium citrate or sodium phosphate, in an amount of 0.1 to 1.0 percent by weight; dyestuffs, such as fluorescein sodium salt, in an amount of about 0.10 to 1.0 percent by weight; care materials, such as plant and vegetable extracts, protein and silk hydrolyzates, lanolin derivative compounds, in an amount of from 0.1 to 5% by weight; physiologically compatible silicone derivative compounds, such as volatile or non-volatile silicone oils or high molecular weight siloxane polymers, in an amount of from 0.05 to 20 percent by weight; light-protective agents, antioxidants, radical-trapping agents, anti-flaking agents, in an amount of from about 0.01 to 2 percent by weight; fatty alcohols, luster-imparting agents, vitamins, softening agents, combability improving substances, defatting agents and anti-foaming agents.

The composition according to the invention can be employed in various application forms. For example, it can be formulated as a lotion, as a non-aerosol spray solution, which is sprayed by means of a mechanical apparatus for spraying, as an aerosol spray which is sprayed by means of a propellant, as an aerosol-foam or as a non-aerosol foam, which is packaged in combination with a suitable mechanical device for foaming the preparation, as a hair cream, as a hair wax, as a gel, as a liquid-gel, as a sprayable gel or as a foaming gel. It is also possible to provide the composition according to the invention in the form of a lotion thickened by a conventional thickener.

If the hair treatment composition according to the invention is provided in the form of an aerosol spray, it contains 15 to 85, preferably 25 to 75, % by weight of a propellant and is filled into a pressurized container. For example, lower alkanes, such as n-butane, i-butane and propanes, or also their mixtures as well as dimethyl ether or fluorinated hydrocarbons, such as F152a (1,1-dichloroethane) or F134 (tetrafluoroethane) can be used as the propellant. Furthermore pressurized gases, such as $N_2$, $N_2O$ and $CO_2$ and their mixtures can also be used as the propellant.

When the hair treatment composition according to the invention is in the form of a sprayable non-aerosol hair spray, it is sprayed with the help of a suitable mechanically driven spraying device. The term "mechanical spraying devices" means those devices, which permit the spraying of a composition without the use of a propellant. These mechanical spraying devices include a spray pump or an elastic container provided with a spray valve. The composition according to the invention is filled under pressure into the elastic container, which stretches so that the composition will be dispensed when the spray valve is opened so that the elastic container contracts.

When the hair treatment composition according to the invention is in the form of hair foam (mousse), at least one common foam-forming substance known for that purpose is included in it. The composition is foamed with or without the aid of a propellant gases or chemical propellants and worked into the hair as a foam which loads the hair without being rinsed out. The composition according to the invention is then used with a device for foaming the composition as an additional part of the invention. Those devices, which permit the foaming of a liquid with or without the use of a propellant, are suitable as foam-forming devices. Suitable mechanical foaming devices can be employed, for example a commercial foam pump or an aerosol foam head.

When the hair treatment composition according to the invention is present in the form of a hair gel, at least one gel-forming substance is present in it in an amount of preferably from 0.05 to 10, especially preferably from 0.1 to 2, percent by weight. The viscosity of the gel amounts to, preferably, from 500 to 50,000 cSt, especially preferably from 1,000 to 15,000 cSt at 25° C. (measured with a rotary viscometer, RheoStress 100 of Haake at a temperature of 25° C. and a shear rate of 0.5 to 1400 $s^{-1}$).

When the hair treatment composition according to the invention is present in the form of a hair wax, it contains a water-insoluble fatty or waxy substance or substances, preferably in an amount of from 0.5 to 30 percent by weight, which impart a wax-like consistency to the composition. Suitable water-insoluble materials are, for example, emulsifiers with an HLB-value under 7, silicone oils, silicone waxes, waxes (e.g. waxy alcohol, waxy acids, waxy esters, and especially natural waxes such as beeswax, carnauba wax, etc), fatty alcohol, fatty acids, fatty ester or high molecular weight polyethylene glycols having a molecular weight of 800 to 20,000, preferably from 2,000 to 10,000, g/mol.

When the hair treatment composition according to the invention is in the form of a hair lotion, it is present as an essentially non-viscose or slightly viscose free flowing solution, dispersion or emulsion with a content of at least 10 percent by weight, preferably 20 to 95 percent by weight, of a cosmetically compatible alcohol. Lower alcohols with 1 to 4 carbon atoms, such as ethanol and isopropanol, are especially suitable for cosmetic purposes.

When the hair treatment composition according to the invention is present in the form of a hair cream, it is preferably an emulsion and additional viscosity imparting substances in an amount of from 0.1 to 10 percent by weight are included in it or the required viscosity and creamy consistency is built up by micell building with the aid of suitable emulsifiers, fatty acids, fatty alcohols, waxes, etc. in the usual way.

The following examples illustrate the subject matter of the invention in further detail. The polymer compound amounts given in the examples are related to the amount of solid materials contained in the composition.

EXAMPLES

Example 1

Comparative Tests

Seventeen polymer solutions were tested. All test solutions contained 3 percent by weight solids content in polymers, 4.5% by weight ethanol and 92.5% by weight water. Polymers containing acid groups were neutralized up to 100% with aminomethylpropanol. The samples E1 to E7 contained on respective single polymers in an amount of 3% by weight. The samples K1 to K10 contained combinations of two of these polymers in an amount of 1.5% by weight of each polymer. The samples K4 to K10 were not of the invention and the samples K1 to K3 were compositions according to the present invention. The following polymers and polymer combinations were tested:

E1: Aquaflex® SF 40 (PVP/vinyl caprolactam/DMAPA acrylates copolymer)
E2: Luviset® CA 66 (VA/crotonates copolymer)
E3: Luvimer® 100 P(tert.-butylacrylate/ethylacrylate/methacrylic acid terpolymer)
E4: Amphomer® (Octylacrylamide/acrylates/butylaminoethyl methacrylate copolymer)
E5: PVP K80 (polyvinylpyrrolidone)
E6: PVP VA 64 (Polyvinylpyrrolidone/vinyl acetate copolymer)
E7: Gaffix® 713 (Vinyl caprolactam/PVP/dimethylaminoethyl methacrylate copolymer)
K1: Aquaflex® SF 40+Luviset® CA66
K2: Aquaflex® SF 40+Luvimer® 100 P
K3: Aquaflex® SF 40+Amphomer®
K4: Aquaflex® SF 40+Gaffix® 713
K5: Luviset® CA 66+PVP K 80
K6: Luvimer® 100 P+PVP K 80
K7: Amphomer®+PVP K 80
K8: Luviset® CA 66+PVP VA 64
K9: Luvimer® 100 P+PVP VA 64
K10: Amphomer®+PVP VA 64

Three respective standardized counted hair strands were used for each test sample for the measurements. A counted hair strand had 100 individual hairs (European hair, 7.5 cm in length, average diameter 73.36 microns, bundle weight, 2.78 mg, color, 5/0, from Kerling). The measurements were performed on unbleached strands after washing with a standard shampoo (10% sodium lauryl ether sulfate, 4% NaCl, 0.5 ml/g hair). The respective strands dried at 20° C. and 65% relative humidity were placed in corresponding folded foils and moistened with equal amounts of water. Subsequently 30 microliters of each of fixing solution was delivered to a respective strand to be tested and the foil was closed around it. After 10 minutes acting time the strands were dried again at 20° C. and 65% relative humidity over night. Three strands were tested during each test. Three breaking force measurements were performed on each strand to be tested at different positions on the strand, of course at the beginning, middle and end of the strand. The measured values in each test were thus the average of nine measurements. The measurement principle or method for measurement of the breaking force is described in the following and in F. Frosch, F. Vogel, 6$^{th}$ International hair Science Symposium of the German Wool Research Institute, Lüneburg, Germany (1988), German Wool Res. Inst. Publ. of Abstracts and in "Assessment of Polymers for Hair Setting", Spray Technology & Marketing, May, 1994, p. 28.

Method of Measurement of Breaking Force

The measurement was performed with a breaking force measurement apparatus. The hair strands were placed with their ends on two supporting elements. A pin or peg coupled to a force sensor gauge is arranged above the strand so as to bear on the strand. The pin is moved down at constant speed with a motor and the strand is bent between the supporting elements (three point-bending test). At the same time the force, which is required, in order to break through the individual hairs of the strand is measured with the force sensor gauge connected with the pin. The force strength signal is transmitted from the testing unit to a controlling processor by means of an IEEE interface and a force-displacement diagram is produced. The force, which is needed, in order to break through the individual hairs of the strand, increases continuously until a maximum value is reached, until the polymer film found on the hairs or the cross-linking of the individual hairs with each other is broken and then it subsequently falls. The observed maximum value of the force-displacement diagram corresponds to the breaking force and is a measure of the fixing strength of the tested composition.

When the break through test is repeated at the same position on the strand, a reduced breaking force is measured, since some of the polymer connections between the individual hair fibers have been irreversibly broken. The less this breaking force has dropped in repeat tests at the same position, the more elastic is the polymer film or the polymeric connections between the individual hairs. The repeat breaking force after repeated break through experiments at the same location on the strand is thus a measure of the elasticity. The elasticity factor E results from a measured first breaking force B1 during a first break through and a subsequent second breaking force B2 of a second break through experiment at the same location. This elasticity factor is given by the following:

$$E = \{B2/B1\} \times 100\%.$$

The results for the breaking force measurement for the first breakthrough experiment B1 and for the second break through experiment B2 as well as the resulting elasticity factor D are tabulated in Table 1 below for the foregoing polymeric compositions. The values set forth for the breaking force are the result of respective measurement values from nine measurements (three different measurements for 3 strands at the three different positions).

TABLE I

BREAKING FORCE AND ELASTICITY RESULTS FOR THE TESTED POLYMERIC COMPOSITIONS

| Sample | B1 [N] | B2 [N] | E [%] |
|--------|--------|--------|-------|
| E1 | 0.51 | 0.19 | 37 |
| E2 | 0.31 | 0.13 | 43 |

TABLE I-continued

BREAKING FORCE AND ELASTICITY RESULTS FOR THE TESTED POLYMERIC COMPOSITIONS

| Sample | B1 [N] | B2 [N] | E [%] |
|--------|--------|--------|-------|
| E3  | 0.34 | 0.13 | 37 |
| E4  | 0.52 | 0.21 | 40 |
| E5  | 0.37 | 0.17 | 46 |
| E6  | 0.24 | 0.11 | 46 |
| E7  | 0.60 | 0.21 | 35 |
| K1  | 0.27 | 0.13 | 49 |
| K2  | 0.31 | 0.14 | 45 |
| K3  | 0.37 | 0.16 | 42 |
| K4  | 0.48 | 0.18 | 36 |
| K5  | 0.35 | 0.16 | 45 |
| K6  | 0.42 | 0.16 | 37 |
| K7  | 0.58 | 0.20 | 35 |
| K8  | 0.27 | 0.11 | 43 |
| K9  | 0.34 | 0.13 | 39 |
| K10 | 0.33 | 0.12 | 37 |

The polymer combination K1 according to the invention has an elasticity factor E=49% and is clearly above that for the individual polymers E1 (37%) and E2 (43%). The polymer combination K2 according to the invention has an elasticity factor E=45% and thus lies clearly above that for the individual polymers E1 (37%) and E3 (37%). The polymer combination K3 according to the invention has an elasticity factor E=42% and thus lies clearly above that for the individual polymers E1 (37%) and E2 (42%). In all cases there is a synergistic increase in the elasticity factor for the combinations of the polymer compounds according to the invention in comparison to that for the compositions containing the individual polymer compounds.

The elasticity factors for the polymer combinations K4 to K10 which are not of the invention are either between those for the individual polymer compounds or even below them. The polymer combinations which are not according to the invention are characterized only by either additive or even antagonistic behavior in regard to the elasticity.

Example 2

Hair Spray

| | |
|---|---|
| 3.335 g | Aquaflex ® SF 40 (PVP/vinyl caprolactam/DMAPA acrylate copolymer) |
| 3.335 g | Octylacrylamide/acrylic acid/butylaminoethyl-methacrylate/methylmethacrylate/hydroxypropyl-methacrylate copolymer (Amphomer ® LV 71) |
| 0.59 g | aminomethylpropanol 95% |
| 0.20 g | perfume |
| 0.02 g | Baysilon ® oil PD 5 |
| 10.00 g | water |
| to 100 g | ethanol |

The effective ingredient containing solution was filed in an aerosol can in a ratio of 45:55 with DME as propellant.

Example 3

Hair Spray

| | |
|---|---|
| 3.335 g | Aquaflex ® SF 40 (PVP/vinyl caprolactam/DMAPA acrylate copolymer) |
| 3.335 g | vinyl acetate/crotonic acid copolymer (Luviset ® CA 66) |
| 0.378 g | aminomethylpropanol 95% |
| 0.20 g | perfume |

-continued

| | |
|---|---|
| 0.02 g | Baysilon ® oil PD 5 |
| 10.00 g | water |
| to 100 g | ethanol |

The effective ingredient containing solution was filed in an aerosol can in a ratio of 45:55 with DME as propellant.

Example 4

Hair Spray

| | |
|---|---|
| 3.335 g | Aquaflex ® SF 40 (PVP/vinyl caprolactam/DMAPA acrylate copolymer) |
| 3.335 g | t-butylacrylate/ethylacrylate/methacrylic acid copolymer (Luvimer ® 100P) |
| 0.844 g | aminomethylpropanol 95% |
| 0.20 g | perfume |
| 0.02 g | Baysilon ® oil PD 5 |
| 10.00 g | water |
| to 100 g | ethanol |

The effective ingredient containing solution was filed in an aerosol can in a ratio of 45:55 with DME as propellant.

Example 5

Aerosol-Foam-Fixing Composition

| | |
|---|---|
| 2.1 g | Aquaflex ® SF 40 (PVP/vinyl caprolactam/DMAPA acrylate copolymer) |
| 0.6 g | vinyl acetate/crotonic acid copolymer (Luviset ® CA 66) |
| 0.07 g | aminomethylpropanol 95% |
| 8.9 g | ethanol |
| 0.4 g | PEG 25 PABA |
| 0.2 g | Laureth-4 |
| 0.2 g | panthenol |
| 0.2 g | perfume |
| 0.07 g | cetyl trimethylammonium chloride |
| 4 g | propane |
| 4 g | butane |
| to 100 g | water |

Example 6

Aerosol-Foam-Fixing Composition

| | |
|---|---|
| 1.5 g | Aquaflex ® SF 40 (PVP/vinyl caprolactam/DMAPA acrylate copolymer) |
| 0.5 g | alkylmonoester of polymethylvinyl ether/maleic acid copolymer (Gantrez ® ES 425) |
| 0.186 g | aminomethylpropanol 95% |
| 8.9 g | ethanol |
| 0.4 g | PEG 25 PABA |
| 0.2 g | Laureth-4 |
| 0.15 g | Betaine |
| 0.15 g | perfume |
| 0.07 g | cetyl trimethylammonium chloride |
| 4 g | propane |
| 4 g | butane |
| to 100 g | water |

Example 7

Sprayed Fixing Composition

| | |
|---|---|
| 1.5 g | Aquaflex ® SF 40 (PVP/vinyl caprolactam/DMAPA acrylate copolymer) |
| 0.45 g | vinyl acetate/crotonic acid/polyethylene oxide copolymer (Aristoflex ® A) |
| 27 g | ethanol |
| 0.7 g | PEG 25 PABA |
| 0.35 g | panthenol |
| 0.25 g | perfume |
| 0.21 g | PEG 40 hydrogenated castor oil |
| 0.20 g | cetyl trimethylammonium chloride |
| to 100 g | water |
| to 100 g | ethanol |

Example 8

Pumped Foam-Fixing Composition

| | |
|---|---|
| 1.3 g | Aquaflex ® SF 40 (PVP/vinyl caprolactam/DMAPA acrylate copolymer) |
| 0.3 g | vinyl acetate/crotonic acid copolymer (Luviset ® CA 66) |
| 0.04 g | aminomethylpropanol 95% |
| 8.9 g | ethanol |
| 0.4 g | cocamidopropyl hydroxysultaine |
| 0.15 g | perfume |
| 0.1 g | citric acid |
| 0.1 g | betaine |
| to 100.00 g | water |

Example 9

Pumped Foam-Fixing Composition

| | |
|---|---|
| 1.5 g | Aquaflex ® SF 40 (PVP/vinyl caprolactam/DMAPA acrylate copolymer) |
| 0.4 g | acrylic acid/ethylacrylate/N-tert-butylacrylamide copolymer (Ultrahold ® 8) |
| 0.037 g | aminomethylpropanol 95% |
| 8.9 g | ethanol |
| 0.4 g | cocamidopropyl hydroxysultaine |
| 0.15 g | perfume |
| 0.1 g | citric acid |
| 0.1 g | betaine |
| to 100.00 g | water |

Example 10

Pumped Foam-Fixing Composition

| | |
|---|---|
| 1.2 g | Aquaflex ® SF 40 (PVP/vinyl caprolactam/DMAPA acrylate copolymer) |
| 0.35 g | t-butylacrylate/ethylacrylate/methacrylic acid copolymer (Luvimer ® 100P) |
| 0.09 g | aminomethylpropanol 95% |
| 8.9 g | ethanol |
| 0.4 g | cocamidopropyl hydroxysultaine |
| 0.15 g | perfume |
| 0.1 g | citric acid |
| 0.1 g | betaine |
| to 100.00 g | water |

The disclosure in German Patent Application 199 57 947.4-43 of Dec. 2, 1999 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a polymer ingredient combinations for hair treatment compositions, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. An aqueous, alcoholic or aqueous-alcoholic hair treatment composition comprising a polymer combination in an aqueous, alcoholic or aqueous-alcoholic cosmetic base, wherein said polymer combination consists of at least one terpolymer of vinyl pyrrolidone, vinyl caprolactam and a basic acrylamide monomer and at least one anionic or anionizable polymer compound having anionic or anionizable groups;

whereby a synergistic effect between said at least one terpolymer and said at least one anionic or anionizable polymer provides improved elasticity to hair with said polymer combination when the hair treatment composition is applied to said hair.

2. The aqueous, alcoholic or aqueous-alcoholic hair treatment composition as defined in claim 1, wherein said at least one anionic or anionizable polymer is selected from the group consisting of polymers of radically polymerizable ethylenic unsaturated carboxylic acid monomers and copolymers of radically polymerizable ethylenic unsaturated carboxylic acid monomers.

3. The aqueous, alcoholic or aqueous-alcoholic hair treatment composition as defined in claim 1, wherein said at least one anionic or anionizable polymer is selected from the group consisting of polymers of acrylic acid, polymers of methacrylic acid, polymers of crotonic acid, polymers of maleic acid, polymers of maleic acid anhydride, polymers of maleic acid monoesters, copolymers of acrylic acid, copolymers of methacrylic acid, copolymers of crotonic acid, copolymers of maleic acid, copolymers of maleic acid anhydride and copolymers of maleic acid monoesters.

4. The aqueous, alcoholic or aqueous-alcoholic hair treatment composition as defined in claim 1, further comprising at least one nonionic film-forming polymer.

5. The aqueous, alcoholic or aqueous-alcoholic hair treatment composition as defined in claim 1, in the form of a lotion, a non-aerosol spray lotion, an aerosol hair spray including a propellant, an aerosol foam including a propellant and a non-aerosol foam.

6. An aqueous, alcoholic or aqueous-alcoholic hair treatment composition comprising a polymer combination in an aqueous, alcoholic or aqueous-alcoholic cosmetic base, wherein said polymer combination consists of at least one terpolymer of vinyl pyrrolidone, vinyl caprolactam and a basic acrylamide monomer and at least one anionic or anionizable polymer compound having anionic or anionizable groups;

wherein said at least one anionic or anionizable polymer is selected from the group consisting of polymers of acrylic acid, polymers of methacrylic acid, polymers of crotonic acid, polymers of maleic acid, polymers of maleic acid anhydride, polymers of maleic acid monoesters, copolymers of acrylic acid, copolymers of methacrylic acid, copolymers of crotonic acid, copolymers of maleic acid, copolymers of maleic acid anhydride and copolymers of maleic acid monoesters.

7. The aqueous, alcoholic or aqueous-alcoholic hair treatment composition as defined in claim 1 or 6, wherein said basic acrylamide monomer is selected from the group consisting of dialkylaminoalkyl-methacrylamides with alkyl groups having from 1 to 4 carbon atoms and dialkylaminoalkylacrylamides with alkyl groups having from 1 to 4 carbon atoms.

8. An aqueous, alcoholic or aqueous-alcoholic hair treatment composition comprising a polymer combination in an aqueous, alcoholic or aqueous-alcoholic cosmetic base, wherein said polymer combination consists of at least one terpolymer of vinyl pyrrolidone, vinyl caprolactam and a basic acrylamide monomer and at least one anionic or anionizable polymer compound having anionic or anionizable groups;

wherein said at least one anionic or anionizable polymer is selected from the group consisting of polymers of acrylic acid, polymers of methacrylic acid, polymers of crotonic acid, polymers of maleic acid, polymers of maleic acid anhydride, polymers of maleic acid monoesters, copolymers of acrylic acid, copolymers of methacrylic acid, copolymers of crotonic acid, copolymers of maleic acid, copolymers of maleic acid anhydride and copolymers of maleic acid monoesters;

whereby a synergistic effect between said at least one terpolymer and said at least one anionic or anionizable polymer provides improved elasticity to hair with said polymer combination when the hair treatment composition is applied to said hair.

9. The aqueous, alcoholic or aqueous-alcoholic hair treatment composition as defined in claim 1, 6 or 8, wherein said cosmetic base includes at least one cosmetic ingredient selected from the group consisting of anionic surfactants, cationic surfactants, amphoteric surfactants, nonionic surfactants, thickeners, perfume ingredients, moisturizers, pearlescence-imparting ingredients, bactericidal ingredients, fungicidal ingredients, buffer substances, coloring ingredients, care materials, physiologically compatible silicon compounds, light-protective agents, antioxidants, radical-trapping substances, anti-flaking ingredients, fatty-alcohols, luster-imparting agents, vitamins, softeners, defatting agents, anti-foaming agents and defatting agents.

10. The hair treatment composition as defined in claim 1, 6 or 8, containing from 1.3 to 5 percent by weight of said at least one terpolymer and from 0.3 to 5 percent by weight of said at least one anionic or anionizable polymer compound.

11. The aqueous, alcoholic or aqueous-alcoholic hair treatment composition as defined in claim 8, wherein said basic acrylamide monomer is selected from the group consisting of dialkylaminoalkylmethacrylamides with alkyl groups having from 1 to 4 carbon atoms and dialkylaminoalkylacrylamides with alkyl groups having from 1 to 4 carbon atoms.

12. The aqueous, alcoholic or aqueous-alcoholic hair treatment composition as defined in claim 8, further comprising at least one nonionic film-forming polymer.

13. The aqueous, alcoholic or aqueous-alcoholic hair treatment composition as defined in claim 8, in the form of a lotion, a non-aerosol spray lotion, an aerosol hair spray including a propellant, an aerosol foam including a propellant and a non-aerosol foam.

* * * * *